US012806206B2

(12) United States Patent
Geng et al.

(10) Patent No.: US 12,806,206 B2
(45) Date of Patent: Nov. 24, 2026

(54) PREPARATION METHOD AND USE OF A NOVEL TAXANE-BASED COMPOUND

(71) Applicant: Jiangsu Jibeier Pharmaceutical Co., Ltd., Zhenjiang (CN)

(72) Inventors: Zhongyi Geng, Jiangsu (CN); Xiugen Wu, Jiangsu (CN); Zhaoguang Li, Jiangsu (CN); Liyun Nie, Jiangsu (CN); Jun Liu, Jiangsu (CN)

(73) Assignee: Jiangsu Jibeier Pharmaceutical Co., Ltd., Zhenjiang (CN)

( * ) Notice: Subject to any disclaimer, the term of this patent is extended or adjusted under 35 U.S.C. 154(b) by 257 days.

(21) Appl. No.: 18/841,551

(22) PCT Filed: Sep. 5, 2023

(86) PCT No.: PCT/CN2023/116986

§ 371 (c)(1),
(2) Date: Aug. 26, 2024

(87) PCT Pub. No.: WO2024/212430

PCT Pub. Date: Oct. 17, 2024

(65) Prior Publication Data

US 2026/0174763 A1 Jun. 25, 2026

(30) Foreign Application Priority Data

Apr. 13, 2023 (CN) ......................... 202310391449.4

(51) Int. Cl.
*A61K 31/519* (2006.01)
*C07D 401/12* (2006.01)
*C07D 487/04* (2006.01)

(52) U.S. Cl.
CPC .......... *A61K 31/519* (2013.01); *C07D 401/12* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 6,096,909 | A | 8/2000 | Ojima |
| 6,319,939 | B1 | 11/2001 | Mabire et al. |
| 2009/0306014 | A1 | 12/2009 | Ballatore et al. |

FOREIGN PATENT DOCUMENTS

| | | | |
|---|---|---|---|
| CN | 103479613 | A | 1/2014 |
| CN | 104116729 | A | 10/2014 |
| CN | 110551080 | A | 12/2019 |
| CN | 111196790 | | 5/2020 |
| CN | 116375668 | A | 7/2023 |
| WO | WO-95/11247 | A1 | 4/1995 |
| WO | WO-2012/088433 | A1 | 6/2012 |

OTHER PUBLICATIONS

Yanhuang et al., “Sdanenu Modern Research and Applications,” Chinese Medical Press, 1st Edition, Jan. 31, 2014, p. 145, with English translation.

Wang et al., “A novel docetaxel derivative exhibiting potent anti-tumor activity and high safety in preclinical animal models,” Biomaterials Science, Aug. 24, 2022, 10(17):4876-4888.

*Primary Examiner* — Samantha L Shterengarts
(74) *Attorney, Agent, or Firm* — Foley & Lardner LLP

(57) ABSTRACT

The present disclosure provides a novel taxane-based compound having a structure represented by Formula (I), a preparation method thereof, and a use thereof in preparation of anti-tumor drugs.

(I)

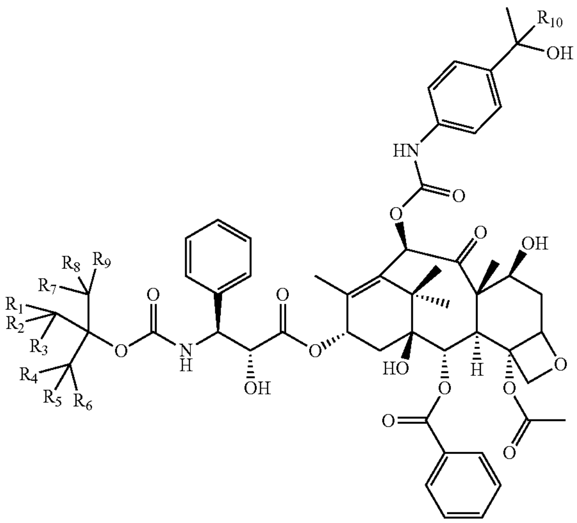

16 Claims, 1 Drawing Sheet

PREPARATION METHOD AND USE OF A NOVEL TAXANE-BASED COMPOUND

CROSS-REFERENCE TO RELATED APPLICATION

The present application is the U.S. National Stage of PCT/CN2023/116986, filed Sep. 5, 2023, which claims priority to, and the benefit of Chinese Patent Application No. 202310391449.4, filed on Apr. 13, 2023 filed with the China National Intellectual Property Administration, the entire contents of which are incorporated herein by reference.

TECHNICAL FIELD

The present disclosure provides a use and a preparation method of a novel taxane-based compound having a structure of Formula I.

BACKGROUND

Docetaxel (Brand Name: Taxotere) achieves an anti-tumor function by suppressing microtubule depolymerization and facilitating the synthesis of tubulin dimers. Results of in vitro anti-tumor test demonstrate that the ability to inhibit cell division of docetaxel is twice that of paclitaxel, $IC_{50}$ being 4 to 35 mg/mL, while the tumor cell proliferation inhibition rate of docetaxel reaches 10 times that of paclitaxel. In addition, docetaxel has better water solubility as compared to paclitaxel, thereby increasing intracellular concentration and bioavailability thereof, and extending intracellular retention time (Yuan Jinying et. al., New Anti-cancer Drugs: Paclitaxel and Docetaxel [M] Beijing: Chemical Industry Press). The structural formula of docetaxel is:

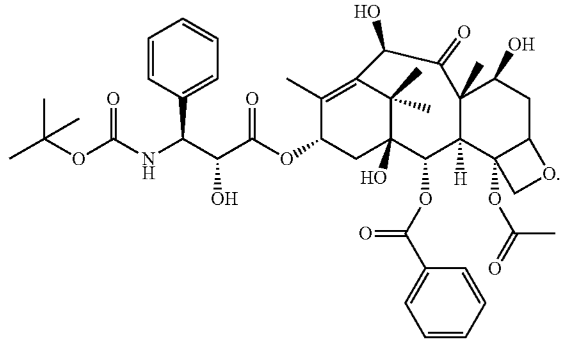

Since 1995 when docetaxel was approved, docetaxel has been launched gradually in over 60 countries including the United States for use in treatment of breast cancer and non-small cell lung cancer, etc. Clinical outcome demonstrated that docetaxel was effective against advanced breast cancer, non-small cell lung cancer, ovarian cancer, pancreatic cancer, liver cancer, head and neck cancers, and the like, reaching an effective rate of 60% against advanced breast cancer, 31% against advanced non-small cell lung cancer, and 30% against advanced ovarian cancer.

Inventors of the present disclosure have been dedicated to structural modification of docetaxel. Formula (I) represents a novel taxane-based drug obtained by structural modification based on the structure of docetaxel and primary efficacy screening. The efficacy research results demonstrated a significant improvement in the efficacy and a significant reduction of toxic and side effects in nude mice models. The novel taxane-based drug was found capable of eliminating tumors (achieving a tumor inhibition rate of above 99%), without tumor recurrence being discovered in the post-withdrawal observation period. The above result was verified in lung cancer A549, liver cancer HepG2, and pancreatic cancer Panc-1 models. Wide use of the novel taxane-based drug of the present disclosure could be anticipated in clinical treatment of relevant diseases.

(I)

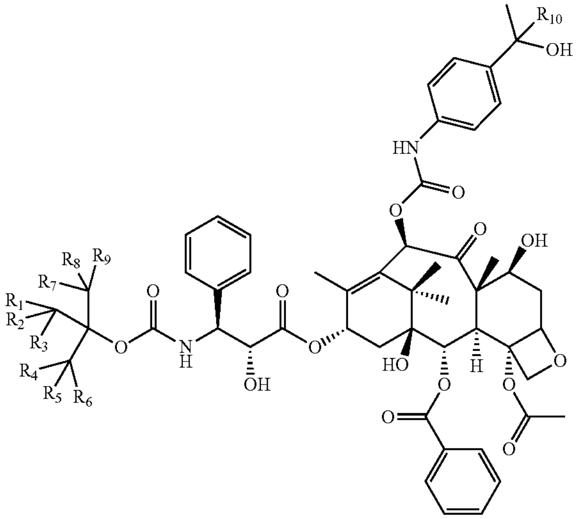

SUMMARY

A first aspect of the present disclosure provides a taxane-based compound with a novel structure, specifically the taxane-based compound represented by Formula (I), or a pharmaceutically acceptable salt or solvate thereof:

(I)

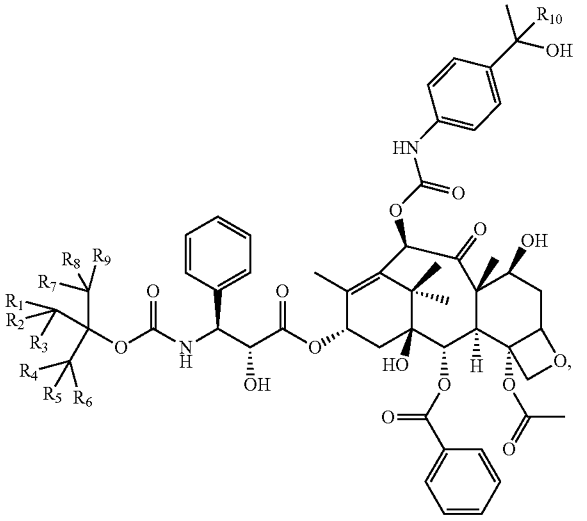

wherein each of $R_1$, $R_2$, $R_3$, $R_4$, $R_5$, $R_6$, $R_7$, $R_8$, $R_9$, and $R_{10}$ is independently hydrogen or deuterium.

In some embodiments, $R_1$, $R_2$, $R_3$, $R_4$, $R_5$, $R_6$, $R_7$, $R_8$, $R_9$, and $R_{10}$ are all hydrogen.

In some embodiments, one or more of $R_1$, $R_2$, $R_3$, $R_4$, $R_5$, $R_6$, $R_7$, $R_8$, $R_9$, and $R_{10}$ are deuterium, or one, three, four, six, seven, nine, or ten of $R_1$, $R_2$, $R_3$, $R_4$, $R_5$, $R_4$, $R_7$, $R_8$, $R_9$, and $R_{10}$ are deuterium.

In some embodiments, $R_1$, $R_2$, $R_3$, $R_4$, $R_5$, $R_6$, $R_7$, $R_8$, and $R_9$ are all hydrogen, and $R_{10}$ is deuterium.

In some embodiments, $R_1$, $R_2$, $R_3$, $R_4$, $R_5$, $R_6$, $R_7$, $R_8$, and $R_9$ are all deuterium, and $R_{10}$ is hydrogen.

In some embodiments, $R_1$, $R_2$, and $R_3$ are all deuterium, and $R_4$, $R_5$, $R_6$, $R_7$, $R_8$, $R_9$, and $R_{10}$ are all hydrogen.

In some embodiments, $R_1$, $R_2$, $R_3$, $R_4$, $R_5$, and $R_6$ are all deuterium, and $R_7$, $R_8$, $R_9$, and $R_{10}$ are all hydrogen.

In some embodiments, $R_1$, $R_2$, $R_3$, and $R_{10}$ are all deuterium, and $R_4$, $R_5$, $R_6$, $R_7$, $R_8$, and $R_9$ are all hydrogen.

In some embodiments, $R_1$, $R_2$, $R_3$, $R_4$, $R_5$, $R_4$, and $R_{10}$ are all deuterium, and $R_7$, $R_8$, and $R_9$ are all hydrogen.

In some embodiments, $R_1$, $R_2$, $R_3$, $R_4$, $R_5$, $R_6$, $R_7$, $R_8$, $R_9$, and $R_{10}$ are all deuterium.

A second aspect of the present disclosure provides a preparation method of the above novel taxane-based compound, comprising:

Step (1): obtaining the compound DTX1 represented by Formula IV from docetaxel represented by Formula V as raw material via triethylsilane protection;

Step (2): obtaining the compound DTX2 represented by Formula I via condensation of DTX1 and 4-acetylphenyl isocyanate;

Step (3): subjecting DTX2 to hydrolysis with hydrochloric acid to obtain the compound represented by Formula II (see Patent No. CN111196790A);

Step (4): subjecting the compound represented by Formula II to a reaction in an alcohol-based solvent in the presence of a reducing reagent and/or a deuterated reagent and then subjecting the resultant to post-treatment, thereby preparing the taxane-based compound represented by Formula I,

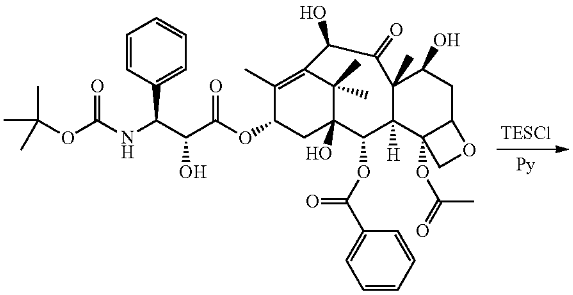

V

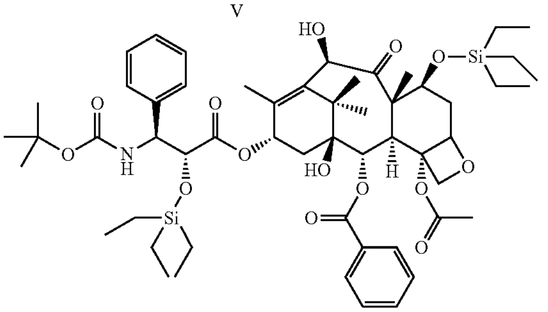

+

IV

-continued

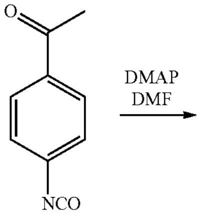

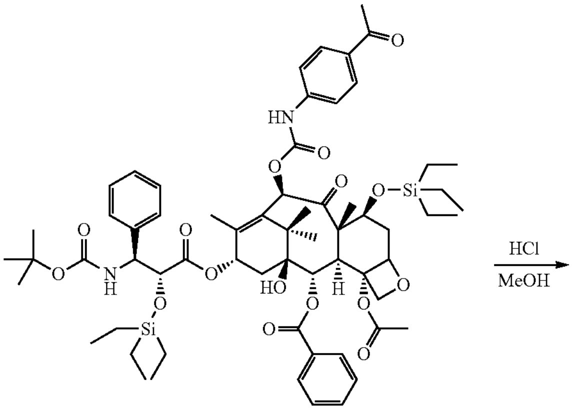

III

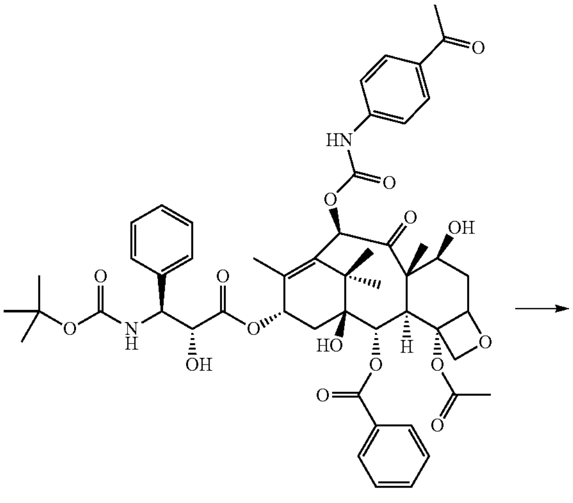

II

-continued

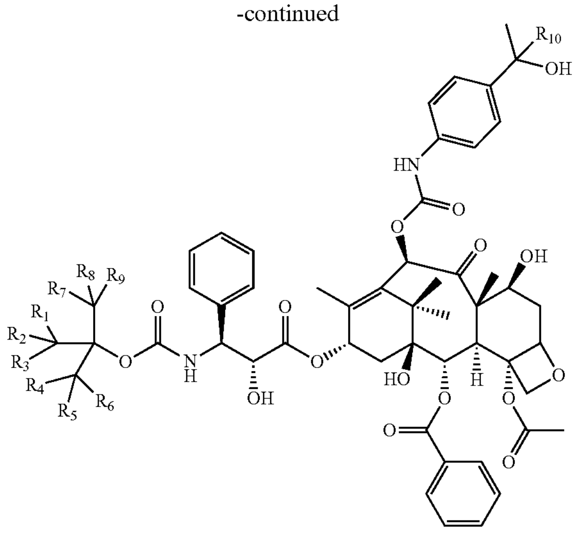

I wherein $R_1$, $R_2$, $R_3$, $R_4$, $R_5$, $R_6$, $R_7$, $R_8$, $R_9$, and $R_{10}$ are as defined in Formula (I).

Further, the reducing reagent is one or more of sodium borohydride, potassium borohydride, lithium borohydride, sodium cyanoborohydride, or sodium triacetoxyborohydride.

Furthermore, the reducing reagent is sodium borohydride.

In some embodiments, the deuterated reagent is

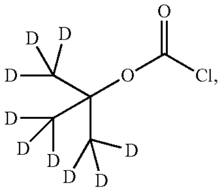

,

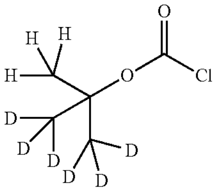

or

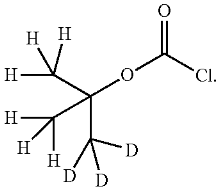

.

Further, a molar ratio of the reducing reagent to the compound of Formula II is (1 to 2):1.

Furthermore, the molar ratio is 1:1.

Further, the alcohol-based solvent is one or more of methanol, ethanol, n-propanol, or isopropanol.

Furthermore, the alcohol-based solvent is methanol.

Further, in the afore-described Step (4), the reaction temperature is −10 to 0° C., and the reaction time is 2 to 3 hours.

Furthermore, the reaction temperature is −10 to −5° C.

Further, the post-treatment is separation through column chromatography or separation through preparative chromatography.

Further, the column chromatography is silica gel column chromatography, and the eluent is a mixture of ethyl acetate and n-hexane, a mixture of dichloromethane and methanol, or a mixture of ethyl acetate and petroleum ether.

Furthermore, the separation through column chromatography uses a silica gel of 100 to 400 mesh, the eluent is a mixture of ethyl acetate and n-hexane in a volume ratio of 1:(1 to 6).

The present disclosure further provides a pharmaceutical composition comprising the taxane-based compound represented by the above Formula (I) or a pharmaceutically acceptable salt or solvate thereof, and a pharmaceutically acceptable excipient and/or carrier.

The present disclosure further provides a use of the taxane-based compound represented by Formula (I) or the pharmaceutically acceptable salt or solvate thereof, or the afore-described pharmaceutical composition in the preparation of anti-tumor drugs.

Preferably, the tumor is eye cancer, rectal cancer, colon cancer, cervical cancer, prostate cancer, breast cancer, bladder cancer, gastric cancer, liver cancer, pancreatic cancer, lung cancer, uterine cancer, ovarian cancer, testicular cancer, kidney cancer, brain cancer, central nervous system cancer, oral cancer, nasopharyngeal cancer, oropharyngeal cancer, hypopharyngeal cancer, laryngeal cancer, cutaneous melanoma, acute lymphoblastic leukemia, acute myeloid leukemia, Ewing's sarcoma, Kaposi's sarcoma, basal cell carcinoma and squamous cell carcinoma, small cell lung cancer, choriocarcinoma, rhabdomyosarcoma, angiosarcoma, hemangioendothelioma, nephroblastoma, neuroblastoma, esophageal cancer, lymphoma, neurofibroma, tuberous sclerosis, hemangioma or lymph cancer.

Advantageous Effect

By the afore-described technical solution, the present disclosure attains to the following advantageous effect:

1) The present disclosure provides a taxane-based compound that inhibits proliferation of various tumor cell lines, and has pharmacological and toxicological properties surpassing those of docetaxel. Compared with docetaxel, it exhibits significant inhibition of tumor cell proliferation and great advantage in pharmacokinetics.
2) The present disclosure provides a preparation method for synthesizing the novel taxane-based compound. The preparation method has the benefits of low cost, high yield, and high purity.

DETAILED DESCRIPTION

Figure 1:
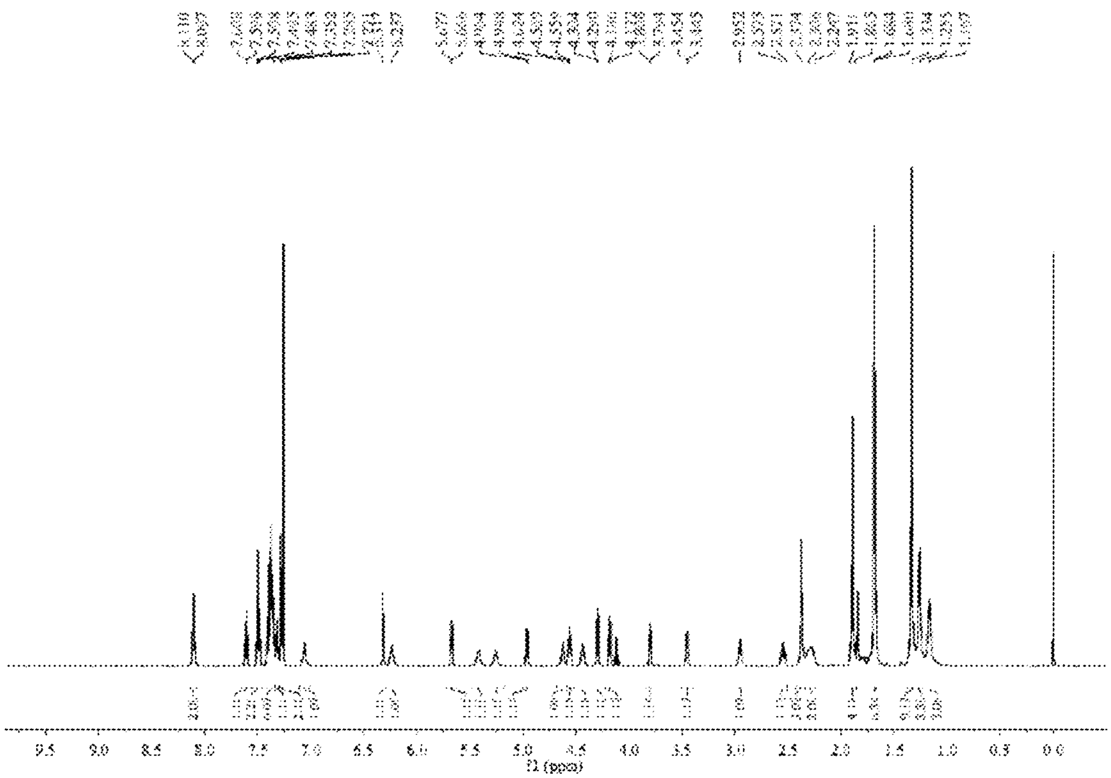
FIG. 1 is a $^1$H-NMR spectrum of the compound of Formula I-1.
Figure 2:
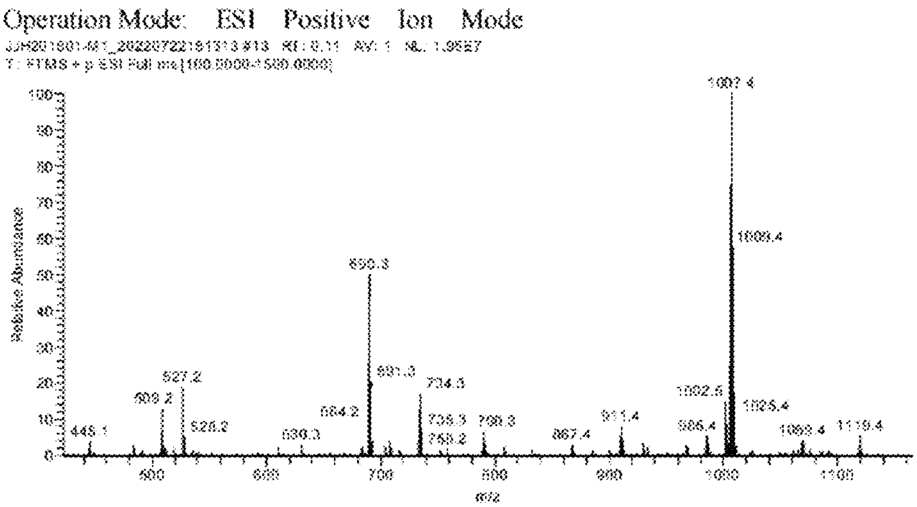
FIG. 2 is an ESI low-resolution mass spectrum of the compound of Formula I-1.

The technical solution of the present disclosure is clearly and completely described subsequently with reference to examples of the present disclosure. Based on the examples of the present disclosure, all additional examples obtained by an ordinary technician in the art without inviting inventive efforts should fall in the scope of protection of the present disclosure.

Based on comprehensive consideration of economy, diversity, and bioactivity of the synthesized compounds, some preferable compounds are listed in the table below. The specific structures thereof are as shown in Table 1. The compounds listed in Table 1 are enumerated in order to better explain the present disclosure, without forming any limitation to the present disclosure. A skilled person in the art appreciates that the scope of the present disclosure on the afore-described subject is not limited to merely the listed compounds.

Formula I

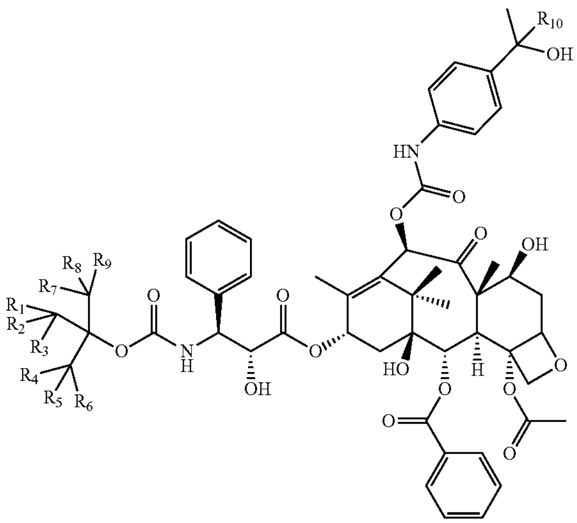

TABLE 1

| Structure of Formula I | | | | | | | | | | |
|---|---|---|---|---|---|---|---|---|---|---|
| Compound No. | $R_1$ | $R_2$ | $R_3$ | $R_4$ | $R_5$ | $R_6$ | $R_7$ | $R_8$ | $R_9$ | $R_{10}$ |
| I-1 | H | H | H | H | H | H | H | H | H | H |
| I-2 | H | H | H | H | H | H | H | H | H | D |
| I-3 | D | D | D | D | D | D | D | D | D | D |
| I-4 | D | D | D | D | D | D | D | D | D | H |
| I-5 | D | D | D | H | H | H | H | H | H | H |
| I-6 | D | D | D | D | D | D | H | H | H | H |
| I-7 | D | D | D | H | H | H | H | H | H | D |
| I-8 | D | D | D | D | D | D | H | H | H | D |

The method for preparing the compound of the present disclosure is explained in the subsequently described technical solution and examples. The raw materials are commercially available or can be prepared by a method known from the literature or as elaborated herein. A person skilled in the art should appreciate that the compound of the present disclosure may be synthesized by other routes of synthesis. Although the specific raw materials and conditions in the routes of synthesis are described subsequently, they can be easily replaced by other similar raw materials and conditions. Various isomers of compounds for example produced by these modifications or variants of the preparation method of the present disclosure are included in the scope of the present disclosure. Additionally, the subsequently described preparation method may be further modified using a conventional chemical method well-known to a person skilled in the art based on the disclosure of the present disclosure. For example, protection may be provided for suitable groups during a reaction process.

Example 1

At room temperature, 20.0 g of docetaxel (DTX) and 100 mL of pyridine were added to a 500-mL three-neck round-bottom flask in sequence, and stirred to dissolution. Under nitrogen gas protection, 12.0 g of triethylchlorosilane (TESCl) was added dropwise with the temperature kept between 20° C. to 30° C. After the addition was completed, the resulting mixture was stirred for 3 hours. 100 mL of water was added thereto, and stirred for 0.5 hours. The resulting mixture was extracted with ethyl acetate (200 mL×3), washed with water and then with saturated brine, dried over anhydrous sodium sulfate for 3.0 hours and then filtered. The filtrate was concentrated to dryness under reduced pressure to obtain 36.4 g of crude product. The nide product was dissolved in 30.0 mL of ethyl acetate, then 180 mL of n-hexane was added dropwise at room temperature. The resulting mixture was stirred and slurried, and then filtered under reduced pressure. After drying under reduced pressure, 21.3 g of DTX1 (a white powdery solid) was obtained with a yield of 89%. $^1$H NMR ($CDCl_3$, 400 MHz) δ: 8.12 (d, J=7.2 Hz, 2H), 7.59 (t, J1=7.2 Hz, J2=7.6 Hz, 1H), 7.48 (t, J=8.0 Hz, J2=8.8 Hz, 2H), 7.37 (t, J1=J2=7.2 Hz, 2H), 7.31-7.27 (m, 3H), 6.33 (t, J1=J2=8.8 Hz, 1H), 5.67 (d, J=7.2 Hz, 1H), 5.48 (d, J=8.8 Hz, 1H), 5.28 (d, J=8.4 Hz, 1H), 5.13 (s, 1H), 4.95 (d, J=8.0 Hz, 1H), 4.55 (s, 1H), 4.41 (dd, J1=6.4 Hz, J2=10.4 Hz, 1H), 4.32 (d, J=8.4 Hz, 1H), 4.27 (s, 1H), 4.20 (d, J=8.8 Hz, 1H), 3.90 (d, J=7.02 Hz, 1H), 2.53 (s, 3H), 2.50-2.44 (m, 1H), 2.38-2.32 (m, 1H), 2.18-2.12 (m, 1H), 1.97-1.90 (m, 4H), 1.75 (s, 3H), 1.61 (s, 1H), 1.31 (s, 9H), 1.27 (s, 3H), 1.16 (s, 3H), 0.94 (t, J=8.0 Hz, 9H), 0.79 (t, J=8.0 Hz, 9H), 0.59-0.54 (m, 6H), 0.45-0.31 (m, 6H).

Example 2

At room temperature, 20.0 g of DTX1, 2.4 g of dimethylaminopyridine (DMAP), and 6.8 g of 4-acetylphenyl isocyanate were added to a 250-mL three-neck round-bottom flask in sequence, followed by the addition of 200 mL of anhydrous tetrahydrofuran. Under nitrogen gas protection, the resulting mixture was heated to 50° C. and stirred for 5 hours at this temperature. After the reaction was completed as monitored by TLC, the reaction solution was cooled and directly concentrated to dryness under reduced pressure to obtain a crude product. The crude product was subjected to separation through column chromatography to obtain 23.5 g of DTX2 as a white solid, with a yield of 87%. Column chromatography condition: petroleum ether ethyl acetate=4:1 to 2:1. $^1$H NMR (400 MHz, $CDCl_3$): 8.12 (d, J=7.6 Hz, 2H), 7.95 (d, J=8.8 Hz, 2H), 7.60-7.53 (m, 4H), 7.48 (t, J1=J2=7.6 Hz, 2H), 7.38 (t, J1=J2=7.6 Hz, 2H), 7.31-7.28 (m, 3H), 6.48 (s, 1H), 6.32 (t, J1=J2=8.8 Hz, 1H), 5.72 (d, J=6.8 Hz, 1H), 5.52 (d, J=9.6 Hz, 1H), 5.31 (d, J=7.2 Hz, 1H), 4.98 (d, J=8.8 Hz, 1H), 4.58 (s, 1H), 4.55-4.51 (dd, J1=10.4 Hz, J2=6.4 Hz, 1H), 4.33 (d, J=8.4 Hz, 1H), 4.21 (d, J=8.4 Hz, 1H), 3.82 (d, J=6.8 Hz, 1H), 2.58 (s, 3H), 2.55 (s, 3H), 2.43-2.37 (m, 1H), 2.23-2.17 (m, 1H), 2.11 (s, 3H), 1.96-1.90 (m, 3H), 1.73 (s, 3H), 1.33 (s, 9H), 1.24 (s, 3H), 1.20 (s, 3H), 0.92 (t, J1=J2=8.0 Hz, 9H), 0.78 (t, J1=J2=8.0 Hz, 9H), 0.64-0.58 (m, 6H), 0.48-0.32 (m, 6H). TOF-MS: calcd for $C_{64}H_{88}N_2O_{16}Si_2$ 1197.5751 [M+H$^+$], found 1197.5739; calcd for $C_{64}H_{88}N_2O_{16}Si_2$ 1219.5570 [M+Na$^+$], found 1219.5587.

Example 3

At room temperature, 20.0 g of DTX2, 50 mL of dichloromethane, and 100 mL of methanol were added to a 5000-mL three-neck round-bottom flask in sequence. The resulting mixture was stirred and dissolved to be clear, then cooled to 5 to 10° C. 35 mL of concentrated hydrochloric acid was added dropwise thereto, and the resulting mixture was stirred and reacted at this temperature for 3 hours. After the reaction was completed as monitored by TLC, saturated sodium bicarbonate solution was added to adjust pH to about 7.0 to 8.0. The resulting solution was subsequently extracted with ethyl acetate (10.0 mL×3), washed with water and then with saturated brine, dried over anhydrous sodium sulfate, and filtered under reduced pressure. The filtrate was concentrated to dryness under reduced pressure to obtain a crude product. The crude product was subjected to column chromatography to obtain 11.8 mg of the compound of Formula II (a white solid), with a yield of 57%. Column chromatography elution condition: petroleum ether:ethyl acetate=2:1 to 1:1. $^1H$ NMR (400 MHz, $CDCl_3$): δ 8.09 (d, J=7.6 Hz, 2H), 7.91 (d, J=8.8 Hz, 2H), 7.61 (t, J1=J2=7.6 Hz, 2H), 7.62-7.59 (m, 4H), 7.39-7.36 (m, 4H), 7.33-7.29 (m, 1H), 6.34 (s, 1H), 6.23 (t, J1=9.2 Hz, J2=5.6 Hz, 1H), 5.47 (d, J=8.4 Hz, 1H), 5.27-5.24 (m, 1H), 4.96 (d, J=9.6 Hz, 1H), 4.63 (br, 1H), 4.47-4.42 (m, 1H), 4.30 (d, J=8.8 Hz, 1H), 4.17 (d, J=8.4 Hz, 1H), 3.80 (d, J=7.2 Hz, 1H), 3.57 (br, 1H), 3.46 (s, 1H), 2.88 (br, 1H), 2.60-2.52 (m, 4H), 2.38 (s, 3H), 2.29-2.27 (m, 2H), 2.00 (m, 1H), 1.90 (s, 3H), 1.87-1.82 (m, 4H), 1.33 (s, 9H), 1.24 (s, 3H), 1.16 (s, 3H). TOF-MS: calcd for $C_{52}H_{60}N_2O_{16}$ 969.4021 [M+H$^+$], found 969.3995.

Example 4

At room temperature, 500 mg of the compound of Formula II was weighed and added to a 100-mL three-neck flask, and then 5 mL of methanol was added thereto. The resulting mixture was stirred to dissolution, then cooled to 0° C., and 20 mg of sodium borohydride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 330 mg of the compound of Formula I-1 as a white powder, with a yield of 66%. $^1H$ NMR ($CDCl_3$, 500 MHz) δ: 8.10 (d, J=6.5 Hz, 2H), 7.61 (t, J1=6.5 Hz, J2=6.0 Hz, 1H), 7.50 (t, J1=6.5 Hz, J2=6.0 Hz, 2H), 7.41-7.35 (m, 6H), 7.33-7.30 (m, 1H), 7.28 (d, J=7.0 Hz, 2H), 7.06 (bra, 1H), 6.32 (s, 1H), 6.24 (m, 1H), 5.67 (d, J=5.5 Hz, 1H), 5.42 (d, J=6.0 Hz, 1H), 5.26 (m, 1H), 4.96 (d, J=8.0 Hz, 1H), 4.62 (s, 1H), 4.56 (t, J1=5.0 Hz, J2=5.5 Hz, 1H), 4.45-4.42 (m, 1H), 4.30 (d, J=7.0 Hz, 1H), 4.18 (d, J=7.0 Hz, 1H), 3.80 (d, J=5.0 Hz, 1H), 3.45 (d, J=4.5 Hz, 1H), 2.95 (s, 1H), 2.57-2.52 (m, 1H), 2.37 (s, 3H), 2.31-2.45 (m, 2H), 1.91-1.87 (m, 4H), 1.68 (m, 6H), 1.33 (s, 9H), 1.26 (s, 3H), 1.17 (s, 3H). LR-ESI: calcd for $C_{52}H_{62}N_2O_{16}$ 1009.4 [M+K$^+$], found 1009.4.

Example 5

At room temperature, 500 mg of the compound of Formula II was weighed and added to a 100-mL three-neck flask, and then 5 mL of methanol was added thereto. The resulting mixture was stirred to dissolution, then cooled to −5° C., and 20 mg of sodium borohydride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 360 mg of the compound of Formula I-1 as a white powder, with a yield of 72%.

Example 6

At room temperature, 500 mg of the compound of Formula U was weighed and added to a 100-mL three-neck flask, and then 5 mL of methanol was added thereto. The resulting mixture was stirred to dissolution, then cooled to −10° C., and 20 mg of sodium borohydride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 420 mg of the compound of Formula I-1 as a white powder, with a yield of 84%.

Example 7

At room temperature, 500 mg of the compound of Formula II was weighed and added to a 100-mL three-neck flask, and then 5 mL of methanol was added thereto. The resulting mixture was stirred to dissolution, then cooled to −5° C., and 20 mg of sodium borodeuteride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 280 mg of the compound of Formula I-2 as a white powder, with a yield of 55%.

Example 8

At room temperature, 500 mg of the compound of Formula II was weighed and added to a 100-mL three-neck flask, and then 5 mL of methanol was added thereto. The resulting mixture was stirred to dissolution, then cooled to −10° C., and 32 mg of sodium cyanoborodeuteride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 320 mg of the compound of Formula I-2 as a white powder, with a yield of 65%.

Example 9

At room temperature, 500 mg of the compound of Formula II was weighed and added to a 100-mL three-neck flask, and then 5 mL of methanol was added thereto. The resulting mixture was stirred to dissolution, then cooled to −10° C., and 12 mg of lithium borodeuteride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 250 mg of the compound of Formula I-2 as a white powder, with a yield of 41%.

Example 10

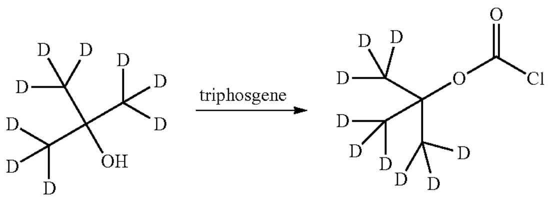

Formula VII Formula VI

At room temperature, 2 g of deuterated tert-butanol (Formula VII) was weighed and added to a 250-mL three-neck flask. The resulting mixture was cooled in an ice-water bath, stirred to dissolution, and then added thereto 4.3 g of triphosgene. After the addition was completed, the resulting mixture was heated to room temperature and stirred until the reaction was completed as monitored by TLC. The reaction solution was concentrated to dryness under reduced pressure to obtain 2.8 g of the compound of Formula VI as a liquid, with a yield of 80%.

Example 11

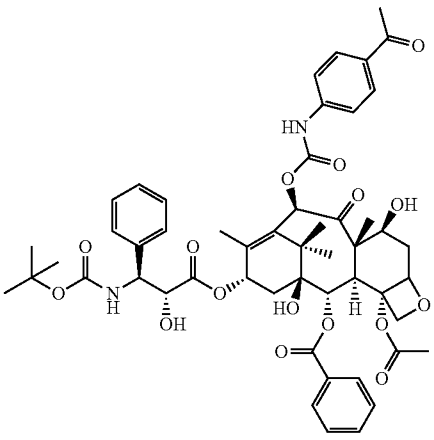
Formula II

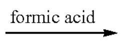

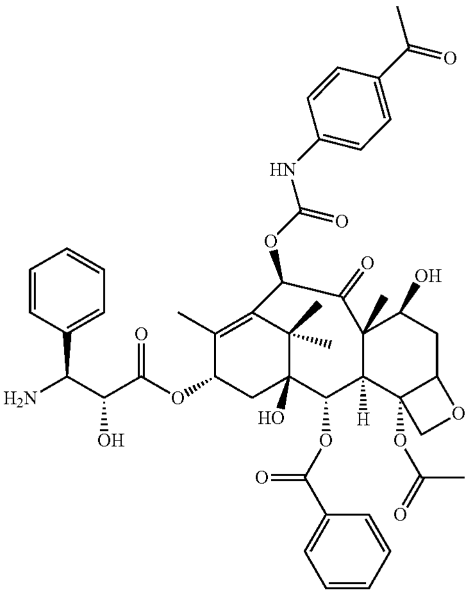
Formula II'

At room temperature, 5 g of the compound of Formula II was weighed and added to a 500-mL three-neck flask, and then added thereto 50 mL of formic acid. The resulting mixture was stirred at room temperature until the reaction was completed as monitored by TLC. The resulting mixture was cooled to 0° C. and slowly added thereto 200 mL of sodium, carbonate solution, then extracted with 200 mL of ethyl acetate. The organic phase was dried over a suitable amount of anhydrous sodium sulfate and filtered. The filtrate was concentrated under reduced pressure and then subjected to separation through column chromatography (ethyl acetate/n-hexane=1:6), obtaining 3.5 g of the compound of Formula II' as a white powder with a yield of 58%.

Example 12

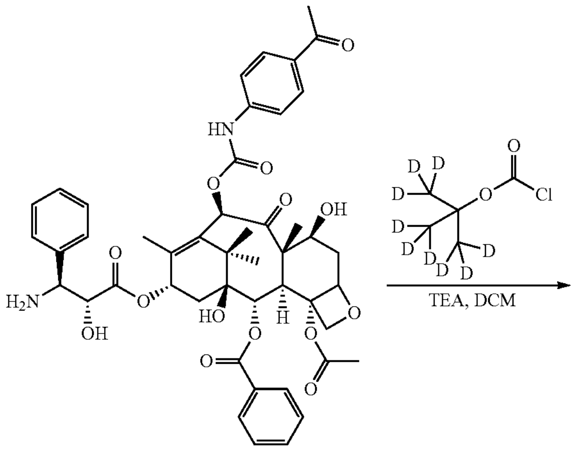

Formula II'

-continued

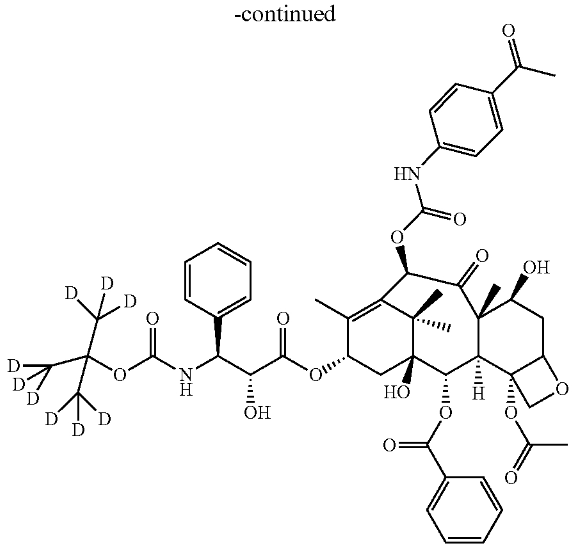

Formula II"

At room temperature, 3 g of the compound of Formula II' was weighed and added to a 250-mL three-neck flask, then added thereto 20 mL of dichloromethane and 5 mL of triethylamine. The resulting mixture was stirred to dissolution, then added thereto 2 g of the compound of Formula VI. The resulting mixture was stirred at room temperature until the reaction was completed as monitored by TLC. The reaction solution was extracted with 200 mL of ethyl acetate and 100 mL of drinking water. The organic phase was dried over a suitable amount of anhydrous sodium sulfate and filtered. The filtrate was concentrated under reduced pressure and then subjected to separation through column chromatography (ethyl acetate/n-hexane=1:6), obtaining 1.6 g of the compound of Formula II" as a white powder with a yield of 46%.

Example 13

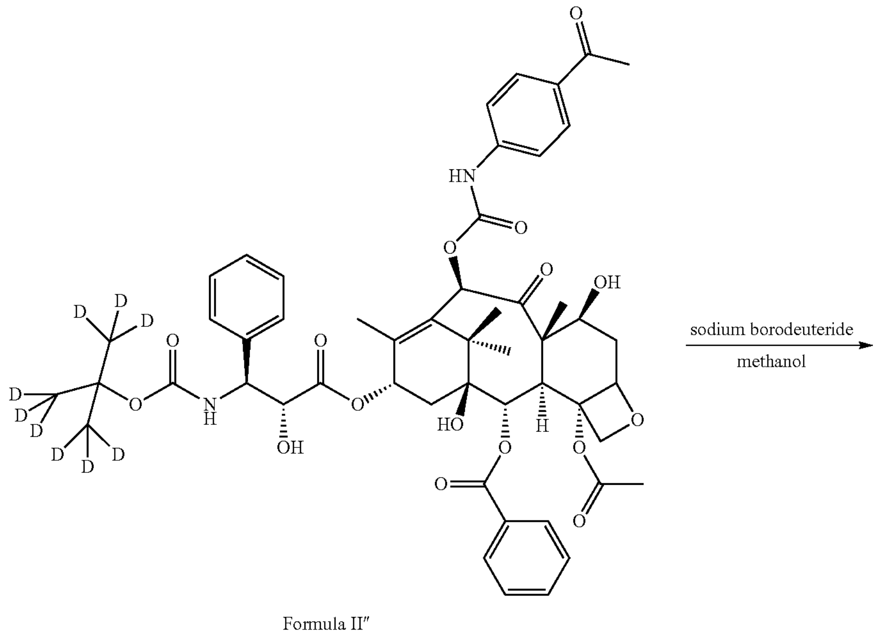

Formula II"

-continued

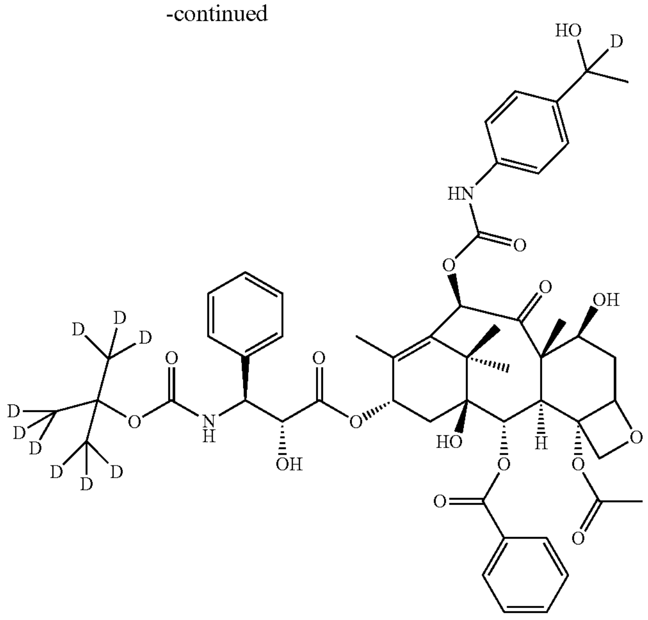

Formula I-3

At room temperature, 500 mg of the compound of Formula II" was weighed and added to a 100-mL three-neck flask, and then 5 mL of methanol was added thereto. The resulting mixture was stirred to dissolution, then cooled to −5° C., and 20 mg of sodium borodeuteride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 240 mg of the compound of Formula I-3 as a white powder, with a yield of 50%.

Example 14

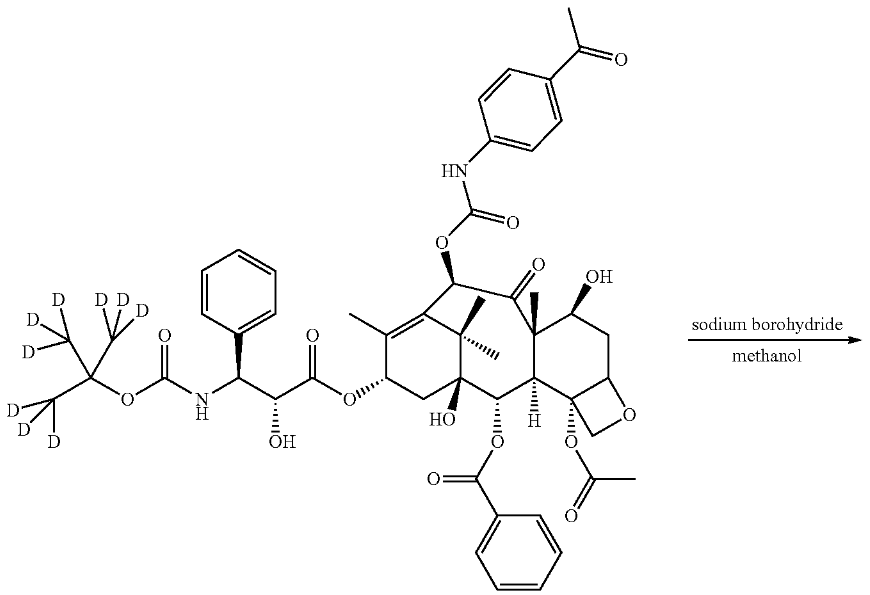

Formula II"

-continued

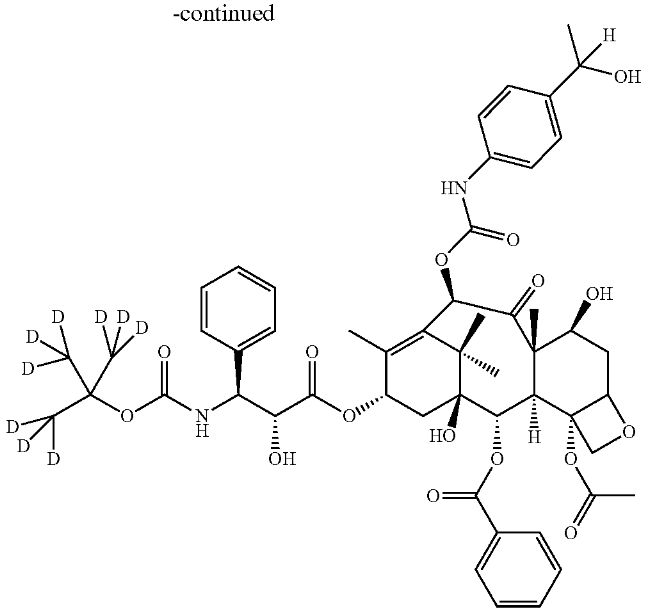

Formula I-4

At room temperature, 500 mg of the compound of Formula II" was weighed and added to a 100-mL three-neck flask, and then 5 mL of methanol was added thereto. The resulting mixture was stirred to dissolution, then cooled to −5° C., and 20 mg of sodium borohydride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 246 mg of the compound of Formula I-4 as a white powder, with a yield of 49%.

Example 15

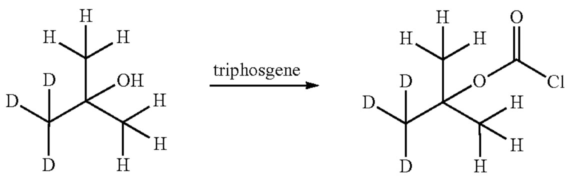

Formula VII′ Formula VI′

At room temperature, 2 g of trideuterated tert-butanol (Formula VII') was weighed and added to a 250-mL three-neck flask. The resulting mixture was cooled in an ice-water bath, stirred to dissolution, and then added thereto 4.3 g of triphosgene. After the addition was completed, the resulting mixture was heated to room temperature and stirred until the reaction was completed as monitored by TLC. The reaction solution was concentrated to dryness under reduced pressure to obtain 3.0 g of the compound of Formula VI' as a liquid, with a yield of 83%.

Example 16

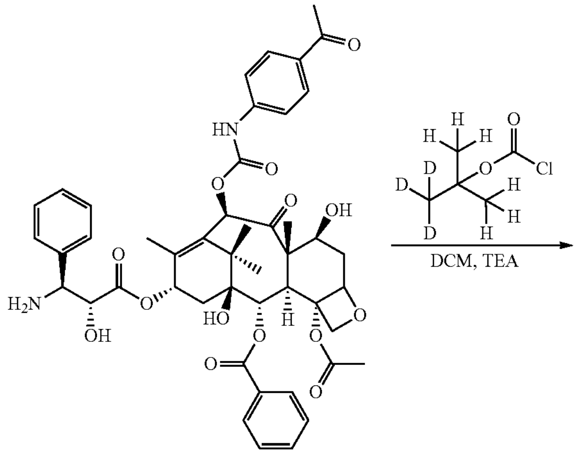

Formula II′

-continued

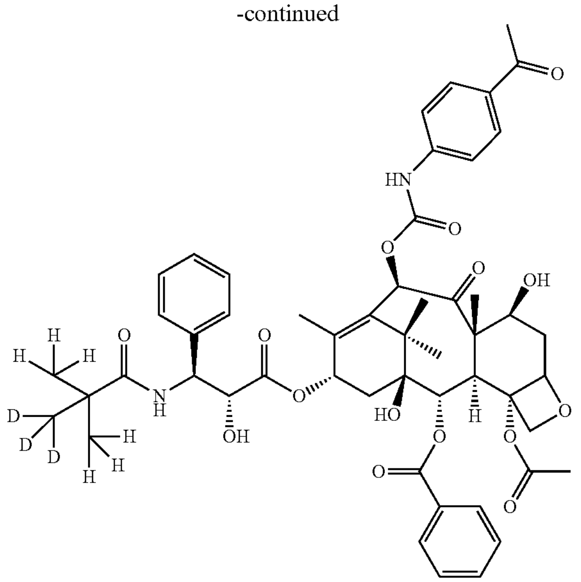

Formula II'''

At room temperature, 3 g of the compound of Formula II' was weighed and added to a 250-mL three-neck flask, then added thereto 20 mL of dichloromethane and 5 mL of triethylamine. The resulting mixture was stirred to dissolution, then added thereto 2 g of the compound of Formula VI'. The resulting mixture was stirred at room temperature until the reaction was completed as monitored by TLC. The reaction solution was extracted with 200 mL of ethyl acetate and 100 mL of drinking water. The organic phase was dried over a suitable amount of anhydrous sodium sulfate and filtered. The filtrate was concentrated under reduced pressure and then subjected to separation through column chromatography (ethyl acetate/n-hexane=1:6), obtaining 1.8 g of the compound of Formula II''' as a white powder with a yield of 55%.

Example 17

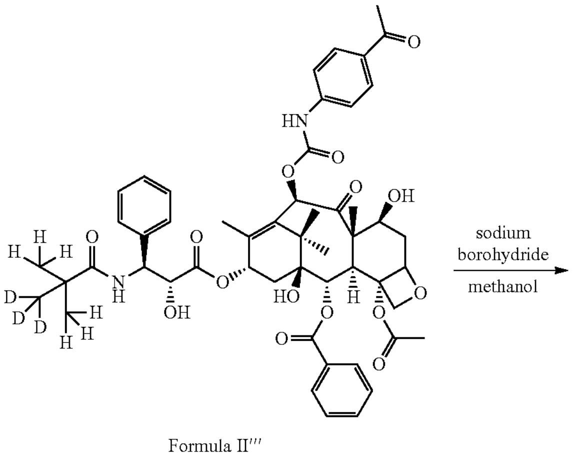

Formula II'''

-continued

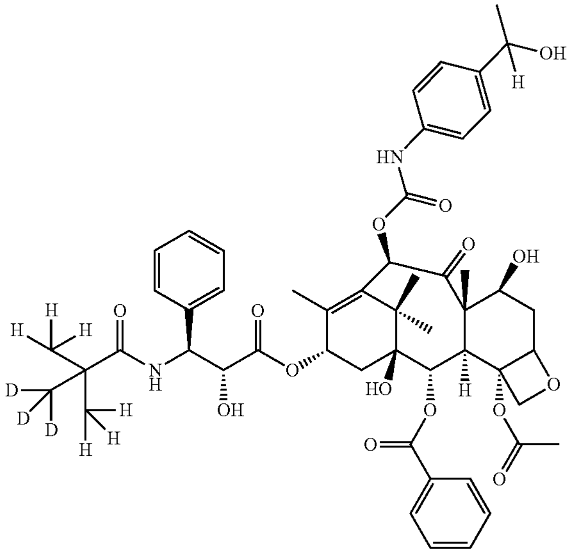

Formula I-5

At room temperature, 500 mg of the compound of Formula II''' was weighed and added to a 100-mL three-neck flask, and then 5 mL of methanol was added thereto. The resulting mixture was stirred to dissolution, then cooled to −5° C., and 20 mg of sodium borohydride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 271 mg of the compound of Formula I-5 as a white powder, with a yield of 54%.

Example 18

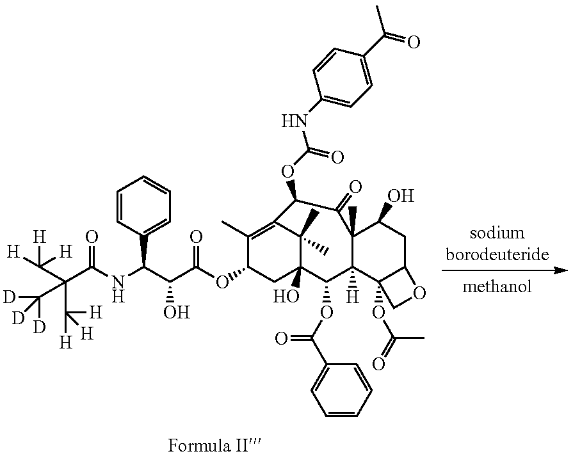

Formula II'''

-continued

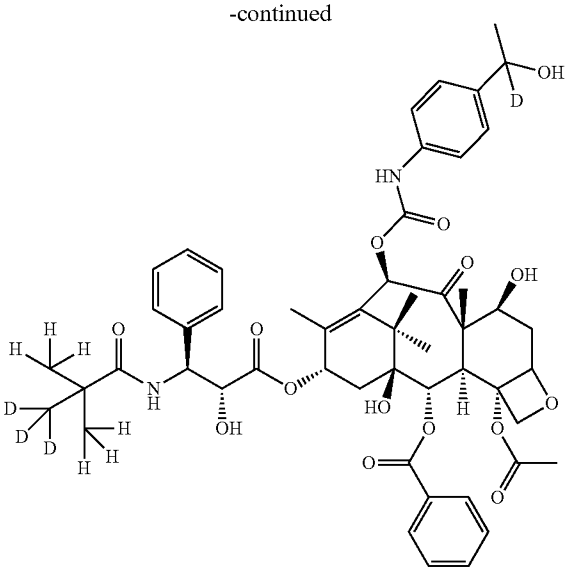

Formula I-7

At room temperature, 500 mg of the compound of Formula II''' was weighed and added to a 100-mL three-neck flask, and then 5 mL of ethanol was added thereto. The resulting mixture was stirred to dissolution, then cooled to −5° C., and 20 mg of sodium borodeuteride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 255 mg of the compound of Formula I-7 as a white powder, with a yield of 51%.

Example 19

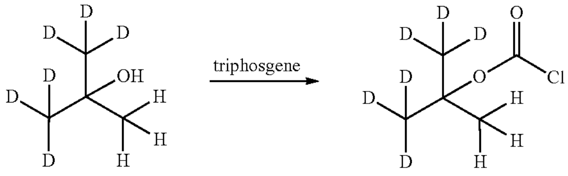

Formula VII'' Formula VI''

At room temperature, 2 g of hexadeuterated tert-butanol (Formula VII'') was weighed and added to a 250-mL three-neck flask. The resulting mixture was cooled in an ice-water bath, stirred to dissolution, and then added thereto 4.3 g of triphosgene. After the addition was completed, the resulting mixture was heated to room temperature and stirred until the reaction was completed as monitored by TLC. The reaction solution was concentrated to dryness under reduced pressure to obtain 2.7 g of the compound of Formula VI'' as a liquid, with a yield of 75%.

Example 20

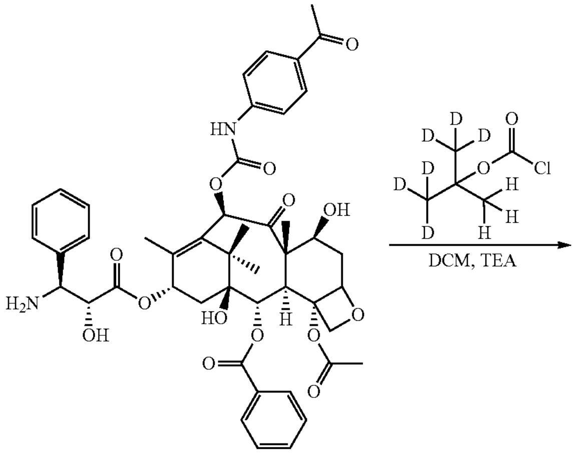

Formula II'

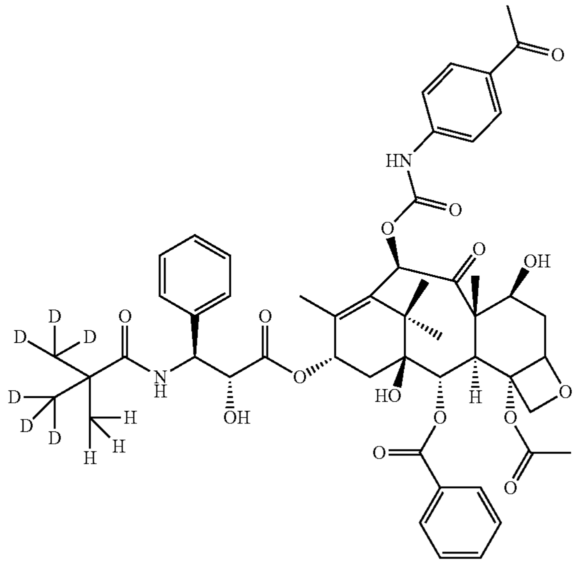

Formula II''''

At room temperature, 3 g of the compound of Formula II' was weighed and added to a 250-mL three-neck flask, then added thereto 20 mL of dichloromethane and 5 mL of triethylamine. The resulting mixture was stirred to dissolution, then added thereto 2 g of the compound of Formula VI''. The resulting mixture was stirred at room temperature until the reaction was completed as monitored by TLC. The reaction solution was extracted with 200 mL of ethyl acetate and 100 mL of drinking water. The organic phase was dried over a suitable amount of anhydrous sodium sulfate and filtered. The filtrate was concentrated under reduced pressure and then subjected to separation through column chromatography (ethyl acetate/n-hexane=1:6), obtaining 2 g of the compound of Formula II'''' as a white powder with a yield of 60%.

Example 21

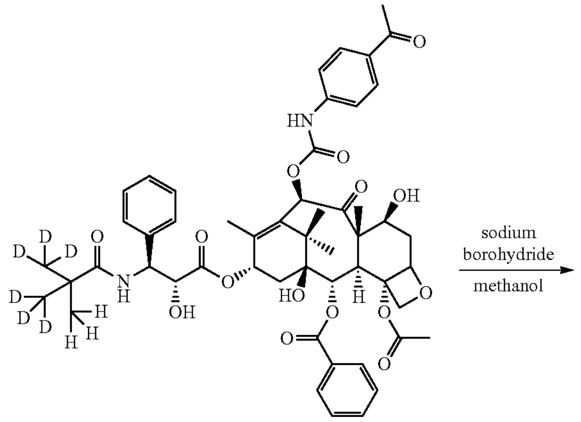

Formula II''''

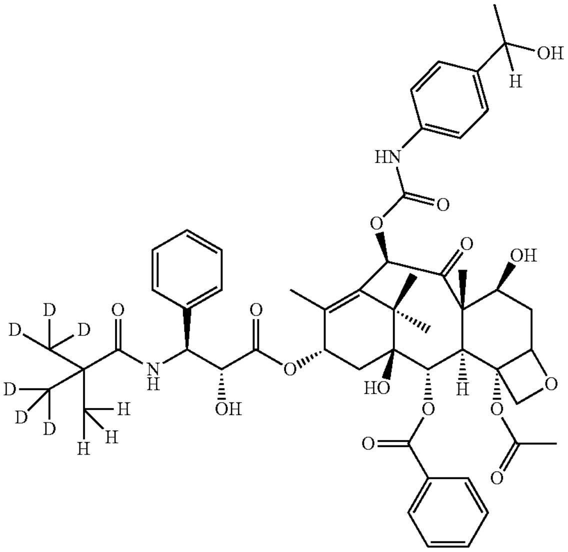

Formula I-6

At room temperature, 500 mg of the compound of Formula II'''' was weighed and added to a 100-mL three-neck flask, and then 5 mL of isopropanol was added thereto. The resulting mixture was stirred to dissolution, then cooled to −5° C., and 20 mg of sodium borohydride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 238 mg of the compound of Formula I-6 as a white powder, with a yield of 47.5%.

Example 22

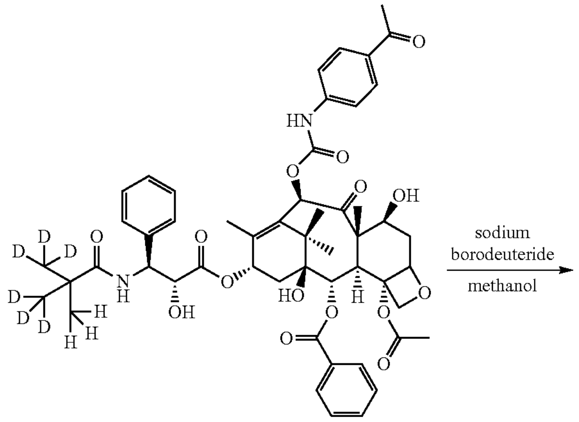

Formula II''''

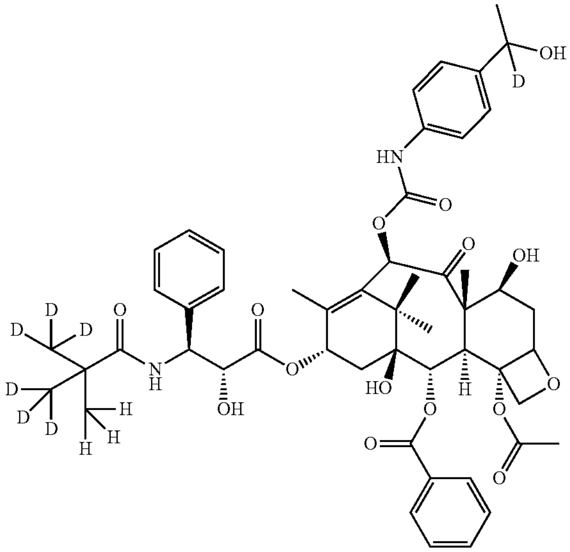

Formula I-8

At room temperature, 500 mg of the compound of Formula II'''' was weighed and added to a 100-mL three-neck flask, and then 8 mL of ethanol was added thereto. The resulting mixture was stirred to dissolution, then cooled to −5° C., and 20 mg of sodium borodeuteride was added thereto. The resulting mixture was stirred at this temperature until the reaction was completed as monitored by TLC. The reaction solution was extracted with 20 mL of ethyl acetate and 20 mL of drinking water. The organic phase was dried over a suitable amount of anhydrous sodium sulfate and then filtered. The filtrate was concentrated under reduced pressure and subjected to separation through column chromatography (200-300 mesh silica gel), with an eluent of ethyl acetate/n-hexane (1:6 to 1:1). The desired eluate was concentrated to dryness under reduced pressure to obtain 266 mg of the compound of Formula I-8 as a white powder, with a yield of 53%.

Example 23

Testing the Inhibition Effect of the Compounds of Formula (I) and Formula II on the Proliferation of Various Tumor Cell Lines by CTG Method:

The CellTiter-Glo Luminescent Cell Viability Assay (CTG) method was used to test the inhibition effect of the compounds of Formula (I) and Formula II on the proliferation of various tumor cell lines, and $IC_{50}$ value was calculated. The tumor cell lines included: human pancreatic cancer cell lines: SW1990, PANC-1, HPAF-II; human gastric cancer cell lines: NCI-N87, MGC-803; human esophageal cancer cell lines: KYSE-150, KYSE-410; human head-and-neck cancer cell lines: C666-1, Fadu; human breast cancer cell line: MDA-MB-231; human lung cancer cell line: A549; human adrenocortical carcinoma cell line: SW-13; human bladder cancer/urothelial carcinoma cell line: BIU-87, totally 13 tumor cell lines.

Experimental method: cells in logarithmic growth phase were obtained. The cell suspension was added to each well of a 96-well plate, placed in an incubator at 37° C. for overnight incubation. Complete mediums corresponding to each of the tumor cell lines were used to dilute the test compounds of Formula (I) and Formula II. The drugs were subjected to gradient dilution according to the following table. Culture medium containing the drug to be tested was added to the 96-well plate. Replicates were provided or each concentration in three wells; and a negative control well not containing the drug to be tested was provided. The 96-well plate was placed in incubator for incubation for 72 h and then added thereto a CTG reagent, with a blank control well provided. The substances in the wells were mixed evenly, and the cells were lysed and incubated at room temperature for 10 min. The fluorescence signal value (Lum) was measured with a microplate reader.

TABLE 1

Gradient dilution concentrations of the test compounds of Formula (I) and Formula II for various tumor cell lines

| Cell names | Drug action concentration (nM) |
|---|---|
| SW1990 | 1000, 333.33, 111.11, 37.04, 12.35, 4.12, 1.37, 0.46, 0.15 |
| PANC-1 | 100, 33.33, 11.11, 3.70, 1.23, 0.41, 0.14, 0.046, 0.015 |
| HPAF-II | 1000, 333.33, 111.11, 37.04, 12.35, 4.12, 1.37, 0.46, 0.15 |
| NCI-N87 | 1000, 333.33, 111.11, 37.04, 12.35, 4.12, 1.37, 0.46, 0.15 |
| MGC-803 | 100, 33.33, 11.11, 3.70, 1.23, 0.41, 0.14, 0.046, 0.015 |
| KYSE-150 | 1000, 333.33, 111.11, 37.04, 12.35, 4.12, 1.37, 0.46, 0.15 |
| KYSE-410 | 1000, 333.33, 111.11, 37.04, 12.35, 4.12, 1.37, 0.46, 0.15 |
| C666-1 | 100, 33.33, 11.11, 3.70, 1.23, 0.41, 0.14, 0.046, 0.015 |
| Fadu | 1000, 333.33, 111.11, 37.04, 12.35, 4.12, 1.37, 0.46, 0.15 |
| MDA-MB-231 | 100, 33.33, 11.11, 3.70, 1.23, 0.41, 0.14, 0.046, 0.015 |
| A549 | 100, 33.33, 11.11, 3.70, 1.23, 0.41, 0.14, 0.046, 0.015 |
| SW-13 | 1000, 333.33, 111.11, 37.04, 12.35, 4.12, 1.37, 0.46, 0.15 |
| BIU-87 | 100, 33.33, 11.11, 3.70, 1.23, 0.41, 0.14, 0.046, 0.015 |

Data processing and analysis: The software GraphPad Prism 8.0 was used to process the data graphically, calculate $IC_{50}$, perform four-parameter non-linear regression analysis on the data, and map the corresponding dose-response curve. The equation for calculating cell viability is as below:

$$\text{cell viability (\%)} = \frac{Lum_{drug-added\ well} - Lum_{blank\ control\ well}}{Lum_{negative\ control\ well} - Lum_{blank\ control\ well}} \times 100$$

Test result: $IC_{50}$ values indicating the inhibition effect of the test compounds on the proliferation of various tumor cell lines are as shown in the table below. It can be seen that the compound of Formula I had a significant activity in inhibiting tumor cell proliferation as compared with the compound of Formula II.

TABLE 2

$IC_{50}$ (nM) of the test compounds for various tumor cell lines

| Cell names | I-1 | I-2 | I-3 | I-4 | I-5 | I-6 | I-7 | I-8 | II |
|---|---|---|---|---|---|---|---|---|---|
| SW1990 | 6.344 | 3.097 | 0.916 | 6.396 | 12.718 | 12.207 | 6.729 | 14.245 | 15.462 |
| PANC-1 | 2.272 | 2.889 | 0.814 | 0.549 | 1.407 | 0.878 | 0.888 | 0.007 | 3.354 |
| HPAF-II | 4.446 | 8.652 | 2.223 | 2.177 | 10.717 | 10.986 | 3.112 | 9.046 | 12.644 |
| NCI-N87 | 28.240 | 7.455 | 8.302 | 18.836 | 11.402 | 12.919 | 10.939 | 14.693 | 20.820 |
| MGC-803 | 0.187 | 3.404 | 2.078 | 4.992 | 0.635 | 3.490 | 4.928 | 0.844 | 5.336 |
| KYSE-150 | 1.994 | 1.753 | 0.376 | 0.726 | 0.808 | 0.123 | 0.972 | 1.697 | 1.896 |
| KYSE-410 | 1.257 | 0.101 | 0.084 | 0.097 | 0.016 | 0.020 | 0.100 | 0.032 | 0.113 |
| C666-1 | 16.026 | 7.339 | 10.484 | 12.069 | 3.394 | 3.033 | 9.189 | 10.471 | 12.754 |
| Fadu | 2.643 | 4.154 | 0.657 | 8.625 | 4.760 | 12.811 | 6.468 | 9.165 | 16.653 |
| MDA-MB-231 | 5.456 | 0.042 | 6.608 | 12.558 | 2.910 | 11.686 | 13.041 | 6.567 | 20.872 |
| A549 | 41.866 | 11.674 | 25.328 | 12.440 | 5.636 | 18.919 | 60.190 | 27.135 | 60.498 |
| SW-13 | 1.568 | 6.119 | 2.686 | 9.116 | 4.754 | 8.480 | 7.357 | 10.138 | 12.544 |
| BIU-87 | 12.081 | 29.062 | 0.319 | 17.508 | 17.721 | 30.148 | 10.195 | 12.697 | 30.457 |

Described in the foregoing are merely preferable examples of the present disclosure. It should be noted that various improvement and modification may occur to an ordinary person skilled in the art without departing from the principle of the present disclosure, and that such improvement and modification should be deemed included in the scope of protection of the present disclosure.

What is claimed is:

1. A taxane-based compound or a pharmaceutically acceptable salt or solvate thereof, wherein a structural formula of the compound is represented by Formula (I), Formula (I)

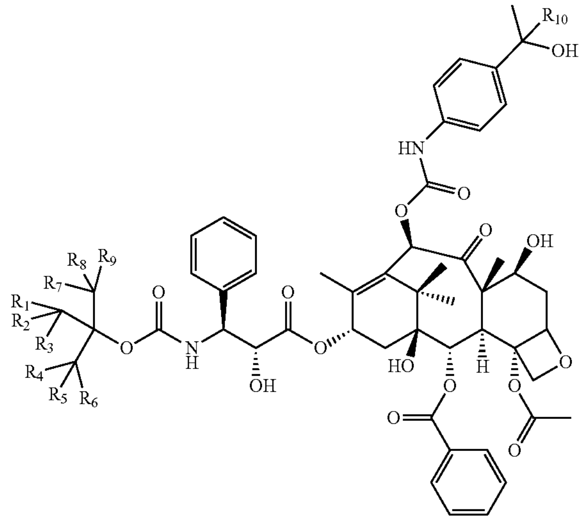

wherein each of $R_1$, $R_2$, $R_3$, $R_4$, $R_5$, $R_6$, $R_7$, $R_8$, $R_9$, and $R_{10}$ is independently hydrogen or deuterium.

2. The taxane-based compound or the pharmaceutically acceptable salt or solvate thereof according to claim 1, wherein one or more of $R_1$, $R_2$, $R_3$, $R_4$, $R_5$, $R_6$, $R_7$, $R_8$, $R_9$, and $R_{10}$ is deuterium;

or $R_1$, $R_2$, $R_3$, $R_4$, $R_5$, $R_6$, $R_7$, $R_8$, $R_9$, and $R_{10}$ are all hydrogen;

or $R_1$, $R_2$, $R_3$, $R_4$, $R_5$, $R_6$, $R_7$, $R_8$, and $R_9$ are all hydrogen, and $R_{10}$ is deuterium;

or $R_1$, $R_2$, $R_3$, $R_4$, $R_5$, $R_6$, $R_7$, $R_8$, and $R_9$ are all deuterium, and $R_{10}$ is hydrogen;

or $R_1$, $R_2$, and $R_3$ are all deuterium, and $R_4$, $R_5$, $R_6$, $R_7$, $R_8$, $R_9$, and $R_{10}$ are all hydrogen;

or $R_1$, $R_2$, $R_3$, $R_4$, $R_5$, and $R_6$ are all deuterium, and $R_7$, $R_8$, $R_9$, and $R_{10}$ are all hydrogen;

or $R_1$, $R_2$, $R_3$, and $R_{10}$ are all deuterium, and $R_4$, $R_5$, $R_6$, $R_7$, $R_8$, and $R_9$ are all hydrogen;

or $R_1$, $R_2$, $R_3$, $R_4$, $R_5$, $R_6$, and $R_{10}$ are all deuterium, and $R_7$, $R_8$, and $R_9$ are all hydrogen;

or $R_1$, $R_2$, $R_3$, $R_4$, $R_5$, $R_6$, $R_7$, $R_8$, $R_9$, and $R_{10}$ are all deuterium.

3. A pharmaceutical composition, comprising the taxane-based compound or the pharmaceutically acceptable salt or solvate thereof of claim 1, and a pharmaceutically acceptable excipient and/or carrier.

4. A preparation method of the taxane-based compound of claim 1, comprising:

Step (1): obtaining a compound represented by Formula (IV) from a compound represented by Formula (V) as raw material via triethylsilane protection;

Step (2): obtaining a compound represented by Formula (III) via condensation of the compound represented by Formula (IV) and 4-acetylphenyl isocyanate;

Step (3): subjecting the compound represented by Formula (III) to hydrolysis with hydrochloric acid to obtain a compound represented by Formula (II);

Step (4): subjecting the compound represented by Formula (II) to a reaction in an alcohol-based solvent in the presence of a reducing reagent and/or a deuterated reagent and then subjecting the resultant to post-treatment, thereby preparing a compound represented by Formula (I),

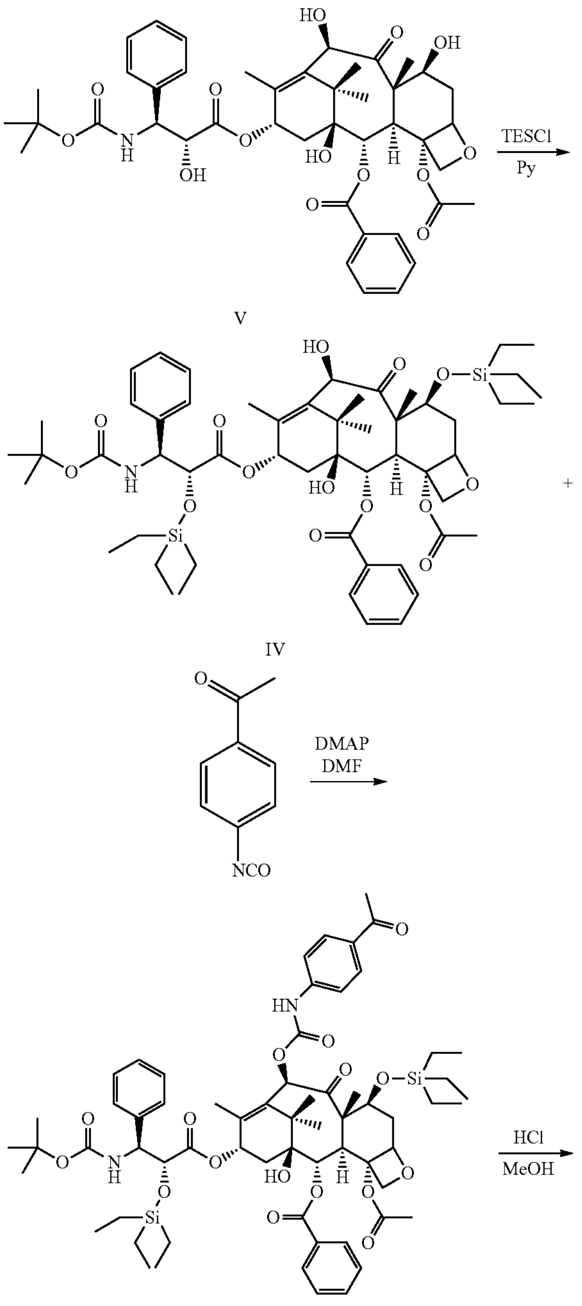

V

IV

III

-continued

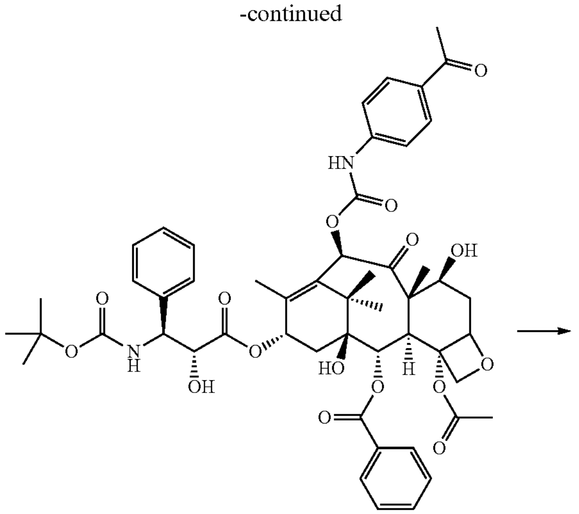

II

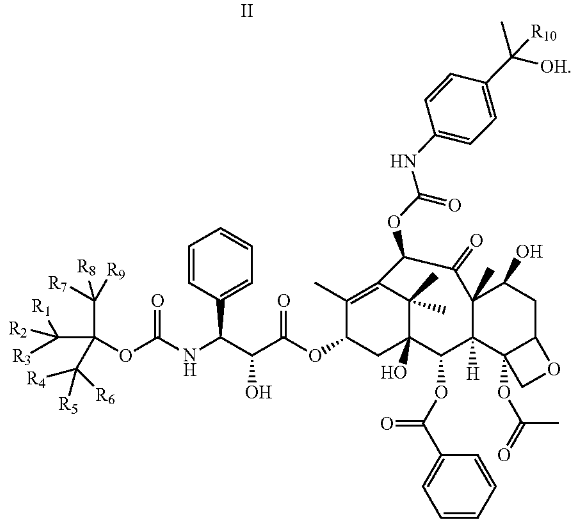

I

5. The preparation method of the taxane-based compound according to claim 4, wherein the reducing reagent is one or more of sodium borohydride, potassium borohydride, lithium borohydride, sodium cyanoborohydride, or sodium triacetoxyborohydride.

6. The preparation method of the taxane-based compound according to claim 5, wherein a molar ratio of the reducing reagent to the compound of Formula II is (1 to 2):1.

7. The preparation method of the taxane-based compound according to claim 4, wherein the alcohol-based solvent is one or more of methanol, ethanol, n-propanol, or isopropanol.

8. The preparation method of the taxane-based compound according to claim 4, wherein in the Step (4), a reaction temperature is −10 to 0° C., and a reaction time is 2 to 3 hours.

9. The preparation method of the taxane-based compound according to claim 4, wherein the post-treatment is separation through column chromatography or separation through preparative chromatography.

10. The preparation method of the taxane-based compound according to claim 4, wherein the reducing reagent is sodium borohydride;

a molar ratio of the reducing reagent to the compound of Formula II is 1:1;

the alcohol-based solvent is methanol; and in the Step (4), a reaction temperature is −10 to −5° C.

11. The preparation method of the taxane-based compound according to claim 9, wherein the column chromatography is silica gel column chromatography, and an eluent is a mixture of ethyl acetate and n-hexane, a mixture of dichloromethane and methanol, or a mixture of ethyl acetate and petroleum ether.

12. The preparation method of the taxane-based compound according to claim 11, wherein a silica gel of 100 to 400 mesh is used in the separation through column chromatography, and the eluent is a mixture of ethyl acetate and n-hexane in a volume ratio of 1:(1 to 6).

13. A method for treating tumor, comprising administering to an individual in need thereof an effective amount of the taxane-based compound or the pharmaceutically acceptable salt or solvate thereof of claim 1.

14. The method according to claim 13, wherein the tumor is eye cancer, rectal cancer, colon cancer, cervical cancer, prostate cancer, breast cancer, bladder cancer, gastric cancer, liver cancer, pancreatic cancer, lung cancer, uterine cancer, ovarian cancer, testicular cancer, kidney cancer, brain cancer, central nervous system cancer, oral cancer, nasopharyngeal cancer, oropharyngeal cancer, hypopharyngeal cancer, laryngeal cancer, cutaneous melanoma, acute lymphoblastic leukemia, acute myeloid leukemia, Ewing's sarcoma, Kaposi's sarcoma, basal cell carcinoma and squamous cell carcinoma, small cell lung cancer, choriocarcinoma, rhabdomyosarcoma, angiosarcoma, hemangioendothelioma, nephroblastoma, neuroblastoma, esophageal cancer, lymphoma, neurofibroma, tuberous sclerosis, hemangioma or lymph cancer.

15. A method for treating tumor, comprising administering to an individual in need thereof an effective amount of the pharmaceutical composition of claim 3.

16. The method according to claim 15, wherein the tumor is eye cancer, rectal cancer, colon cancer, cervical cancer, prostate cancer, breast cancer, bladder cancer, gastric cancer, liver cancer, pancreatic cancer, lung cancer, uterine cancer, ovarian cancer, testicular cancer, kidney cancer, brain cancer, central nervous system cancer, oral cancer, nasopharyngeal cancer, oropharyngeal cancer, hypopharyngeal cancer, laryngeal cancer, cutaneous melanoma, acute lymphoblastic leukemia, acute myeloid leukemia, Ewing's sarcoma, Kaposi's sarcoma, basal cell carcinoma and squamous cell carcinoma, small cell lung cancer, choriocarcinoma, rhabdomyosarcoma, angiosarcoma, hemangioendothelioma, nephroblastoma, neuroblastoma, esophageal cancer, lymphoma, neurofibroma, tuberous sclerosis, hemangioma or lymph cancer.

* * * * *